(12) United States Patent
Hulme

(10) Patent No.: US 8,357,916 B2
(45) Date of Patent: Jan. 22, 2013

(54) FLUORESCENCE MEASUREMENT CELL

(75) Inventor: Keith Hulme, Hainault (GB)

(73) Assignee: Starna Scientific Limited (GB)

( * ) Notice: Subject to any disclaimer, the term of this patent is extended or adjusted under 35 U.S.C. 154(b) by 0 days.

(21) Appl. No.: 12/867,391

(22) PCT Filed: Feb. 16, 2009

(86) PCT No.: PCT/GB2009/000410
§ 371 (c)(1),
(2), (4) Date: Aug. 12, 2010

(87) PCT Pub. No.: WO2009/101422
PCT Pub. Date: Aug. 20, 2009

(65) Prior Publication Data
US 2010/0327182 A1    Dec. 30, 2010

(30) Foreign Application Priority Data
Feb. 14, 2008    (GB) .................................. 0802750.0

(51) Int. Cl.
*G01J 1/58*    (2006.01)
*G01N 21/03*    (2006.01)
(52) U.S. Cl. .................................................. 250/458.1
(58) Field of Classification Search ............... 250/458.1; 356/440
See application file for complete search history.

(56) References Cited

U.S. PATENT DOCUMENTS

| | | | |
|---|---|---|---|
| 4,750,837 A | | 6/1988 | Gifford et al. |
| 5,493,405 A | * | 2/1996 | Hulme .......................... 356/440 |
| 5,757,482 A | * | 5/1998 | Fuchs et al. .................... 356/246 |
| 5,917,606 A | * | 6/1999 | Kaltenbach ..................... 356/440 |
| 5,964,998 A | * | 10/1999 | Kambara ....................... 204/452 |
| 2005/0046834 A1 | * | 3/2005 | Gilby ............................ 356/317 |
| 2005/0140971 A1 | * | 6/2005 | Yamaguchi et al. ........... 356/246 |

FOREIGN PATENT DOCUMENTS

| | | |
|---|---|---|
| EP | 0762119 A | 3/1997 |
| GB | 2280283 A | 1/1995 |
| WO | 02071029 A | 9/2002 |

OTHER PUBLICATIONS

EPO/ISA, International Search Report for corresponding International Application No. PCT/GB2009/000410, mailed May 6, 2009.

* cited by examiner

*Primary Examiner* — Marcus Taningco
(74) *Attorney, Agent, or Firm* — Stites & Harbison, PLLC; David W. Nagle, Jr.; Stephen J. Weyer

(57) ABSTRACT

A cell for measuring the fluorescence of a sample comprising an incident wall surface (2), a sample chamber (6) and an emitting wall member (14) which collimates light though a lens (13). The lens (13) is adapted to collect light from the emitting wall member (14) and direct it towards a detector. In addition, the cell comprises a mirrored surface coating which reflects light back to the sample chamber (6), thereby energising the sample further. The cell is suitable for use with small sample volumes, as a result, it allows significant sample cost savings. In addition, fluorescence detection is enhanced by said mirrored surfaces which prevent emitted light from escaping, moreover, the light is reflected back to the sample, thereby energising it further. The collimated light directed to the detector also provides for more stable and reproducible results and higher detection limits when emission energy is low.

9 Claims, 2 Drawing Sheets

FLUORESCENCE MEASUREMENT CELL

The present invention relates to a cell for measuring the emission spectrum of a sample, particularly but not exclusively a fluid sample.

Cells for spectrometry are typically produced by joining at least two pieces of polished optical material by using heat alone. Consequently, cells are constructed without the use of intermediates or adhesives and are, therefore, completely homogeneous and resistant to all solutions except those which react with the optical material itself. In addition, the production process involves careful annealing of any strain in the cell. Accordingly, the cells can withstand a reasonable amount of physical and thermal shock, ultrasonic vibration and pressure differentials of up to 3 atmospheres. In addition, the cells may be used at extreme temperature if appropriate care is taken. However, in certain circumstances for example where dissimilar materials are used, it is possible to use an adhesive or other materials to bond windows to the cell.

Cells may be constructed from different materials depending on their suitability for different applications, for instance, cells may be constructed from glass, quartz, or plastic materials such as acrylics. The type of material used varies according to the specific application the cell will be utilized in, these applications range from photometry to high pressure liquid chromatography (HPLC). Accordingly, there are various types of cell to be used in the different types of spectrometry. The external dimensions of the cell are determined and restricted by cell-holder dimensions.

In a typical fluorimeter, light produced by a light source passes through an excitation monochromator and an optical system, reaches the front window of the fluorescent cell containing the sample, where it is absorbed by the sample which subsequently emits light of a longer wavelength. The emitted light passes through another monochromator to a detector where the fluorescence is measured. Cells for fluorimetry generally require at least three, preferably four, optically transparent faces because the optical system constituting a fluorimeter is arranged to transmit light into a sample through the front wall of a cell and then detect a fluorescent emission through another wall which is disposed at an angle, generally 90°, to the aforesaid front wall.

Whilst most known cells would work adequately for applications where the sample volume varies from 50 μL to 3500 μL it has become increasingly necessary to manufacture cells for smaller sample volumes that, at the same time, comply with the cell holder external dimensions mentioned above. Nevertheless, this requirement produces a difficulty as sample volumes are greatly variable and volumes as small as 5 μL or less are common in some fields.

In addition, in fluorimetry applications emission energy, that is, the light of longer wavelength emitted by the sample, can be very low, thus small samples add extra difficulty. Further, because the cells have at least three optically transparent walls emissions may exit the cell from three or all sides, as a consequence, sample emissions may not be perceived in their entirety by the detector.

The present invention seeks to provide a fluorimeter cell for fluorescence measurements of samples with a small volume.

According to the invention there is provided a cell for measuring fluorescence of a sample, which cell comprises an incident wall surface, a sample chamber and an emitting wall member characterised in that said wall member is adapted to collimate light though a lens, which lens is adapted to collect light from the emitting wall member and direct it, in use, towards a detector, the cell further comprising a mirrored surface adapted to reflect incident light back towards the sample chamber thereby enabling further energisation of a sample.

In a preferred embodiment of the invention, the cell is constructed by a plurality of blocks of suitable material. In a preferred embodiment, the blocks are fused or bonded to optically transparent wall members. In another embodiment, the cell is constructed by a plurality of walls of suitable material. In a preferred embodiment of the invention, the incident light is reflected back towards the sample chamber by a plurality of mirrored surfaces, thereby enabling further energisation of the sample. In a preferred embodiment of the invention, a lens is included in the emitting wall member. In a preferred embodiment, the lens is integral with the incident wall member. In another embodiment, the lens is fused or bonded to said emitting wall member. In yet another embodiment, an intermediate wall member is located between the emitting wall member and the sample chamber.

When light in a fluorimeter is emitted from a light source, it travels though a monochromator and an optical system and reaches the side wall of the fluorescent cell where it is absorbed by the sample. In the present cell the light emitted by the sample is directed from the end of the window through the lens which collimates the light onto the detector. Consequently, scattered light is collected through a wide cone from the end of the sample compartment and directed towards the detector. Accordingly, the light that was not emitted straight out of the end of the cell, and which would not normally hit the detector because it is at some distance from the sample, is captured.

Furthermore, in a preferred embodiment windows in the back surfaces opposite to the incident light and opposite to the emission window are both at least partially mirrored, as a result, the incident light is reflected back through the sample further energising the fluorescent media and the window opposite the detector that is mirrored reflects back any emission which is going in that direction back to the sample and out of the emission window, therefore, enhancing the amount of light that reaches the detector.

The present cell is effective with small samples because it incorporates at least one mirror-coated window in the walls through which emission may be lost, thereby enhancing detection of the light emitted by the samples.

A further advantage of this set up is that the escaping incident light may be diverted back into the sample, thereby energising it further.

Another advantage of the this set up is that the collimated light directed to the detector provides for more stable and reproducible results and higher detection limits when emission energy is low.

An exemplary embodiments of the invention will now be described with reference to the accompanying drawings, in which.

Figure 1:
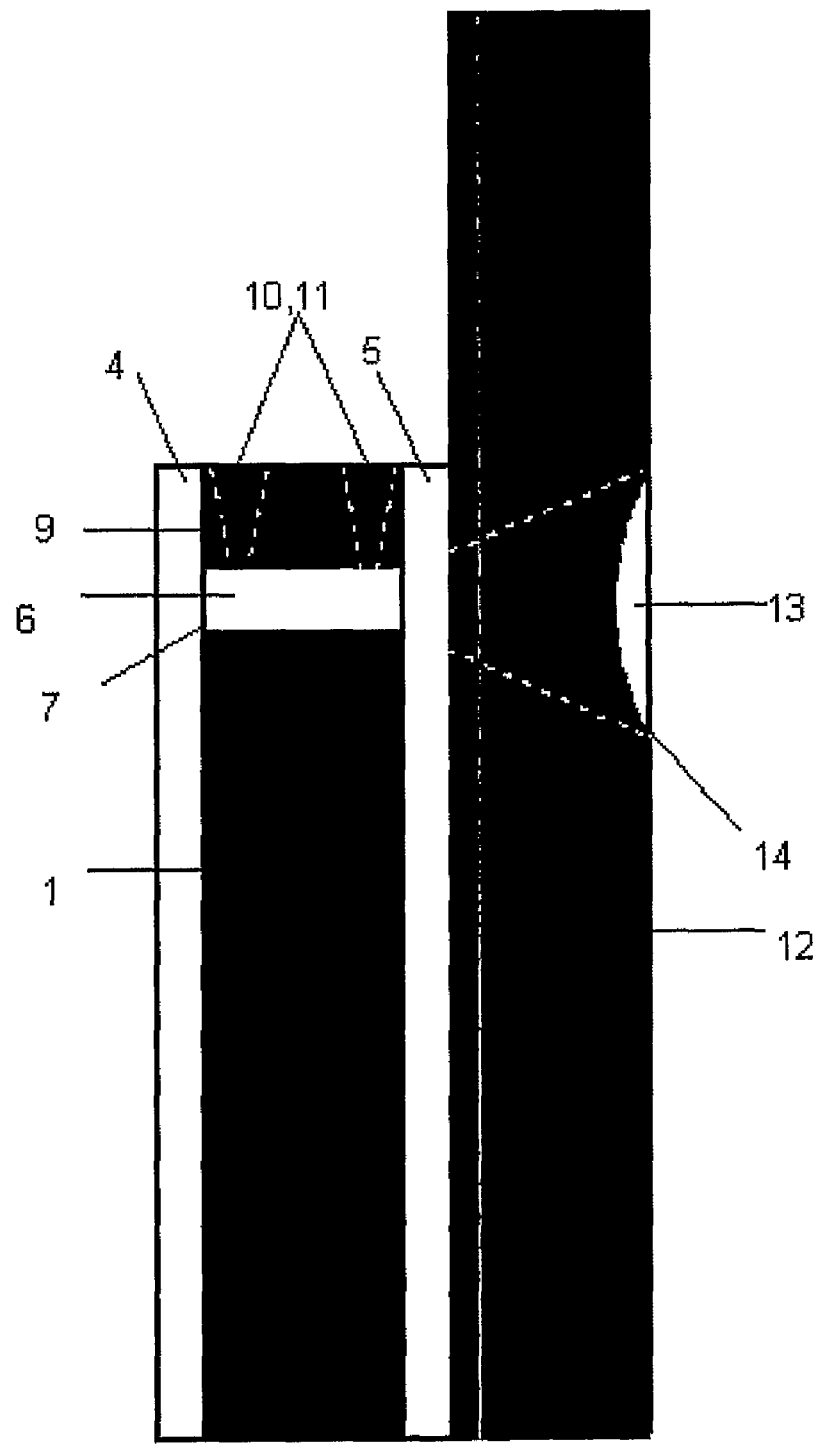
FIG. 1 shows a side view of a fluorescence measurement cell.

FIG. 1 shows a side view of a fluorescence measurement cell comprising a first, rectangular, block 1. In this exemplary embodiment the block 1 is formed from black quartz. A sample chamber 6 is defined by optically transparent sample chamber side members 7, 8, and is located on the top of block 1. Sample chamber side members 7, 8 will typically be fused to block 1. A second black quartz block 9 having inlet 10 and outlet 11 to allow samples to be placed in the chamber 6 or fluid reagents to be passed into or through the chamber, if a study of a reaction is desired, is located on top of the sample chamber 6 and will typically fused to the side members 7, 8. Optically transparent wall members 4, 5 are located on either side of the blocks 1, 9 perpendicular to the blocks 1, 9; wall members 4, 5 will typically be fused to both blocks 1, 9. A third block 12, also in this embodiment formed from black quartz, is fused to the optically transparent wall member 5 and a lens 13 is located in the wall surface remote from the wall member 5 and a passage 14 machined in the quartz block defines an emitting wall member to enable light from the sample chamber 6 to pass to the lens 13. The rectangular block 12 is shown as having a greater height than the combined height of blocks 1, 9 and the sample chamber 6; this arrangement is useful for structural and sample holder alignment reasons but is not essential.

Figure 2:
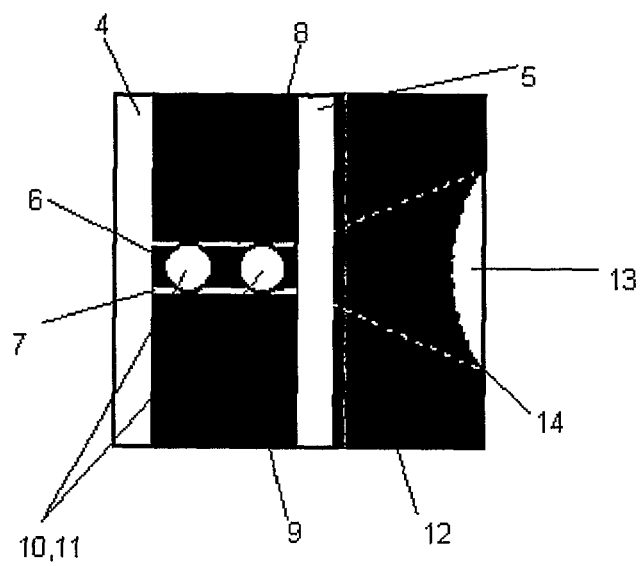
FIG. 2 shows a top view of the fluorescence measurement cell.

FIG. 2 shows a fluorescent cell having a generally rectangular cross-section comprising a rectangular block 9. In this exemplary embodiment the block 9 is formed from black quartz. Said block 9 comprises inlet 10 and outlet 11 ports to enable access to the chamber 6. The block 9 is located on top of the sample chamber 6 and will typically fused to the side members 7, 8. Optically transparent wall members 4, 5 are located on either side of the block 9. Block 12, also in this embodiment formed from black quartz, is fused to the optically transparent wall member 5 and a lens 13 is located in the wall surface remote from the wall member 5 and a passage 14 machined in the quartz block to enable light from the sample chamber 6 to pass to the lens 13.

Figure 3:
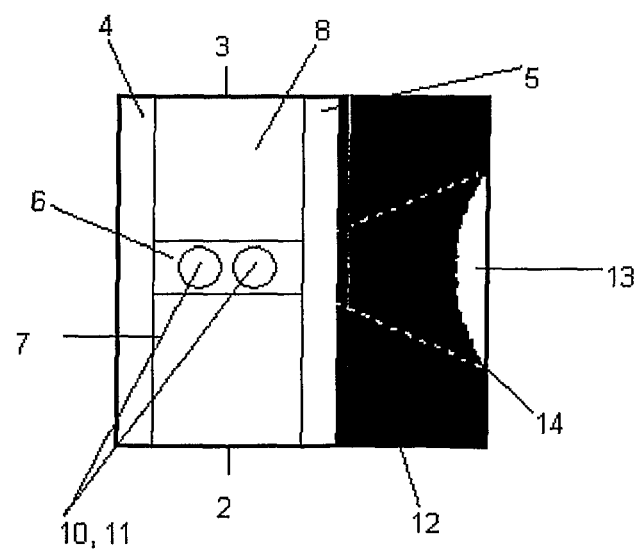
FIG. 3 shows a cross-section view of the fluorescence measurement cell and the sample chamber.

FIG. 3 shows a fluorescent cell having a generally rectangular cross-section comprising a sample chamber 6 defined by optically transparent chamber side members 7, 8 and wall members 4, 5, with the inlet 10 and outlet 11 ports shown encircled. The side member 7 comprises an incident wall surface 2; the side member 8 comprises a parallel rear wall surface 3 spatially remote from the incident wall 2. A mirrored coating adapted to reflect light back into the sample chamber 6 is applied to the rear wall surface 3 and to the surface of the optically transparent wall member 4.

In use, the cell is placed in a standard holder in a fluorimeter and light is incident on the incident wall surface 2 and passes through the chamber 6, where it can interact with a sample in the chamber. Light then exits the chamber 6 via the exit wall 3 and through the optically transparent wall members 4, 5. The mirrored coatings on the wall 3 and wall member 3 then reflect the light back into the sample chamber, where it can further interact with the sample and further energise the fluorescent media. Light exiting through the wall member 5 then passes to the lens 13, which can then collect the emitted light and direct it towards a detector.

Although the cell has been described as having black quartz blocks with the various chambers and apertures machined into them, it would of course be possible to use suitable other materials, which could also simply be fused or bonded depending on the precise application. Alternatively, the cell could be constructed by fusing or bonding plaques of suitable material to form separate walls.

The invention claimed is:

1. A fluorimeter cell for use in a standard fluorimeter cell holder, the fluorimeter cell for measuring fluorescence of a sample, which cell comprises an incident wall surface, a sample chamber, an exit wall, an emitting wall member and a lens, the incident wall and the exiting wall defining two walls of the sample chamber in which a sample is disposed during fluorimetry, wherein, in use, incident light traveling along an incident light pathway enters through the incident wall surface and passes through the sample chamber to energise a sample disposed therein and exits through the exit wall, wherein said wall member and lens are outside the incident light pathway, and the wall member is adapted to collimate light emitted by the sample though the lens, which lens is adapted to collect the light emitted by the sample from the emitting wall member and direct it, in use, towards a detector, the cell further comprising a mirrored wall surface on the exit wall, adapted to reflect incident light back towards the sample chamber thereby enabling further energisation of the sample, and wherein the fluorimeter cell has dimensions for use in a standard fluorimeter holder.

2. The cell according to claim 1, wherein said cell is constructed by a plurality of blocks.

3. The cell according to claim 2, wherein said blocks are fused or bonded to optically transparent wall members.

4. The cell according to claim 1, wherein said cell is constructed by a plurality of walls of suitable material.

5. The cell according to claim 1, wherein incident light is reflected back towards the sample chamber by a plurality of mirrored surfaces on the exit wall, the incident wall member, an optically transparent wall member or a combination thereof, thereby enabling further energisation of the sample.

6. The cell according to claim 1, wherein the lens is integral with the emitting wall member.

7. The cell according to claim 1, wherein the lens is fused or bonded to said emitting wall member.

8. The cell according to claim 1, wherein an intermediate wall member is located between the emitting wall member and the sample chamber.

9. The cell according to claim 1, wherein the incident light pathway is perpendicular to a fluorescence pathway from the sample to the lens.

* * * * *